(12) United States Patent
Cardones et al.

(10) Patent No.: US 10,376,449 B2
(45) Date of Patent: Aug. 13, 2019

(54) FLEXIBLE CONTAINER FOR CONCENTRATED PRODUCT

(71) Applicant: Johnson & Johnson Consumer Inc., Skillman, NJ (US)

(72) Inventors: Michelle Cardones, Jacksonville Beach, FL (US); H. Michael Moscherosch, Doylestown, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 502 days.

(21) Appl. No.: 15/042,481

(22) Filed: Feb. 12, 2016

(65) Prior Publication Data

US 2017/0231877 A1  Aug. 17, 2017

(51) Int. Cl.

| | |
|---|---|
| *A61Q 19/00* | (2006.01) |
| *A61K 8/19* | (2006.01) |
| *A45F 3/16* | (2006.01) |
| *B01D 35/02* | (2006.01) |
| *B01D 41/00* | (2006.01) |
| *B65D 1/02* | (2006.01) |
| *B65D 75/58* | (2006.01) |
| *C02F 1/00* | (2006.01) |

(Continued)

(52) U.S. Cl.
CPC ................ *A61K 8/19* (2013.01); *A45F 3/16* (2013.01); *A61J 1/2089* (2013.01); *A61Q 19/00* (2013.01); *B01D 35/02* (2013.01); *B01D 41/00* (2013.01); *B65D 1/02* (2013.01); *B65D 75/5861* (2013.01); *B65D 75/5872* (2013.01); *B65D 85/816* (2013.01); *C02F 1/002* (2013.01); *A45F 2003/163* (2013.01); *A61K 2800/10* (2013.01); *A61K 2800/30* (2013.01)

(58) Field of Classification Search
CPC ................ A61Q 19/00; A61K 2800/10; A61K 2800/30; A45F 2003/163; B65D 75/5861; B65D 1/02; B65D 75/5872; B65D 85/816; C02F 1/002; A61J 1/2089; B01D 35/02; B01D 41/00
See application file for complete search history.

(56) References Cited

U.S. PATENT DOCUMENTS

| | | |
|---|---|---|
| 2,773,521 A | 3/1954 | Persson |
| 2,775,350 A | 12/1956 | Persson |
| 4,983,286 A | 1/1991 | Inagaki et al. |

(Continued)

FOREIGN PATENT DOCUMENTS

| | | |
|---|---|---|
| EP | 0138681 A2 | 4/1985 |
| WO | WO 2007/086969 A2 | 8/2007 |
| WO | WO 2013057014 A1 | 4/2013 |

OTHER PUBLICATIONS

International Search Report dated Apr. 25, 2017—PCT/US2017/014810.

(Continued)

*Primary Examiner* — Anshu Bhatia
(74) *Attorney, Agent, or Firm* — Laura A. Donnelly

(57) ABSTRACT

Provided are flexible containers for holding a concentrate, the containers comprising: a flexible body holding the concentrate, a spout, a filter element disposed in the spout, the filter element comprising a filter and an attachment element configured to attach to a water source. Also provided are methods of reconstituting concentrated products using the flexible containers.

14 Claims, 11 Drawing Sheets

(51) Int. Cl.
*A61J 1/20* (2006.01)
*B65D 85/816* (2006.01)

(56) References Cited

U.S. PATENT DOCUMENTS

| | | |
|---|---|---|
| 5,273,649 A | 12/1993 | Magnusson et al. |
| 5,431,813 A | 7/1995 | Daniels |
| 5,731,021 A | 3/1998 | Spector |
| 6,165,362 A | 12/2000 | Nohren, Jr. et al. |
| 6,200,471 B1 | 3/2001 | Nohren, Jr. |
| 6,245,228 B1 | 6/2001 | Kelda |
| 6,411,777 B2 | 6/2002 | Roberson |
| 6,641,719 B1 | 11/2003 | Naito |
| 6,656,350 B2 | 12/2003 | Kitakaze |
| 6,766,106 B2 | 7/2004 | Roberson |
| 7,303,683 B2 | 12/2007 | Cumberland |
| 7,404,737 B1 | 7/2008 | Youtsey |
| 7,484,626 B2 * | 2/2009 | Judkins ............... B01D 61/027 210/321.6 |
| 7,810,651 B2 | 10/2010 | Miga, Jr. |
| 8,142,654 B2 | 3/2012 | Kohl |
| 8,197,771 B2 * | 6/2012 | Maiden ............... B01D 29/085 422/501 |
| 8,464,633 B2 | 6/2013 | Anson et al. |
| 8,585,905 B2 | 11/2013 | Mallet |
| 8,845,895 B1 | 9/2014 | Ghiassi |
| 9,045,353 B2 | 6/2015 | Parekh et al. |
| 2003/0127393 A1 | 7/2003 | Tepper et al. |
| 2003/0192909 A1 | 10/2003 | Maskell |
| 2009/0285949 A1 | 11/2009 | Brown |
| 2012/0021108 A1 | 1/2012 | Baumann et al. |
| 2013/0119086 A1 | 5/2013 | Pellingra et al. |
| 2014/0284298 A1 * | 9/2014 | Epars .................. A61J 9/00 215/11.1 |
| 2015/0344323 A1 | 12/2015 | Namin |

OTHER PUBLICATIONS

International Search Report dated Apr. 25, 2017—PCT/US2017/014807.

* cited by examiner

FLEXIBLE CONTAINER FOR CONCENTRATED PRODUCT

FIELD OF THE INVENTION

The present invention relates generally to devices for holding concentrated products and methods for the reconstitution of concentrated products. Specifically, the present invention relates to flexible containers with filter elements for storing and reconstituting concentrated consumer products.

BACKGROUND OF THE INVENTION

Surfactant concentrates are well known in the art. Such concentrates are economical to ship to formulators who dilute the concentration with water or add the concentrates to cleaning compositions for use as a component of shampoos, cleansers, lotions, dishwasher or laundry detergents, etc. Food concentrates may also be dehydrated, shipped to a final destination, and then rehydrated prior to final use.

A recurring problem is that in some locations, such as developing countries or wilderness areas, water sources are often contaminated. In these cases, pretreatment or filtering of the contaminated water is required to decontaminate the water prior to reconstituting the consumer or food product.

There is therefore a desire to ship concentrated products to their final destination, and then, starting with water at the final destination, including in some cases contaminated water, reconstitute the product for consumer use.

SUMMARY OF THE INVENTION

According to one aspect, the present invention provides a flexible container holding a concentrate, the container comprising: a flexible body holding the concentrate, a spout, a filter element disposed in the spout, the filter element comprising a filter and an attachment element configured to attach to a water source.

According to another aspect, provided are methods of reconstituting a concentrated product comprising: providing a flexible container of the claimed invention; attaching a water source to said attachment element of said flexible container; and introducing water from said water source through said filter element and into said flexible container to reconstitute the concentrate.

DETAILED DESCRIPTION OF THE INVENTION

Figure 1:
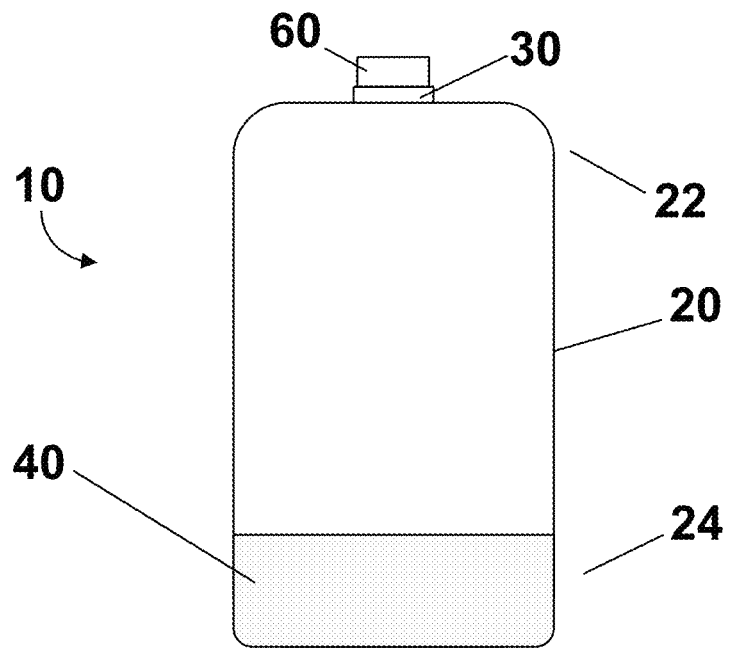
FIG. 1 is a front view of a flexible package according to an embodiment of the present invention.

The term "concentrate" as used herein means the concentrated form of substance to which water or other diluting agent may be added to reconstitute the concentrate to the substance desired. Examples of certain concentrates, according to certain embodiments of the present invention, include concentrated forms of fluid consumer product formulations that may be reconstituted via the addition of water to consumer products intended for use by a consumer.

The term "consumer product" as used herein means merchandise or other items of common or daily use, ordinarily bought by individuals or households for private consumption. A representative, non-limiting list of product categories includes personal care products including products for: baby care including lotions, soaps, shampoos, and conditioners; skin care, including body washes, facial cleansers, hand lotions, moisturizers, conditioners, astringents, exfoliation products, microdermabrasion and peel products, skin rejuvenation products, anti-aging products, masks, and UV protection products; beauty care, such as, cosmetics and colognes; feminine care; hair care (human or animal), including bleaches, colors and dyes, shampoos, conditioners (including rinse-off and leave-in forms), and styling aids; oral care, including toothpaste, dentifrice, tooth gel, tooth rinse, mouth rinse, gum care, denture adhesive, and tooth whitening; personal cleansing, including hand soaps and shower gels. Other product categories include household products including products for: dish care, including hand dishwashing agents or light duty dishwashing agents, and machine dishwashing agents; fabric care, including fabric treatment and conditioning (including softening); laundry care, including detergents, bleach, conditioners, softeners, anti-static products, and liquid refreshers; floor and surface cleaning and/or treatment products, wood floor cleaners, antibacterial floor and surface cleaners, air refreshers and vehicle washing products; as well as healthcare products including over-the-counter products such as respiratory and cough/cold products, pain relievers, oral and topical analgesics, gastro-intestinal treatment products, RX pharmaceuticals, and pet health and nutrition. Food, beverage, and snack products are also included.

The present invention is directed to containers for concentrates, and methods of their use, that can be advantageously used to reconstitute such concentrates from a variety of water sources, including sources of contaminated water. According to certain embodiments, the present invention is directed to a flexible container for a concentrate comprising a flexible body holding the concentrate, a spout, a filter element disposed in the spout, the filter element comprising a filter and an attachment element configured to attach to a water source.

The container of the present invention may be in any form suitable to hold a concentrate and to allow fluid to be added thereto to reconstitute the concentrate within the flexible body. Examples of suitable containers with a flexible body include sachets, pouches, bottles, and the like.

As will be readily understood by one of skill in the art, pouches for use in the present invention may be any suitable spouted pouch. In general, pouches are multi-layered laminates of with printable outer layers and inner layers with barrier properties. Examples of suitable types of spouted pouches include shaped pouches, stand-up pouches, retort pouches, box pouches, slider pouches, zipper pouches, and the like. Pouches may be obtained from manufacturers such as Glenroy, Inc. (Menomonee Falls, Wis.) or ProAmpac (Cincinnati, Ohio).

In certain preferred embodiments, the container of the present invention is a single- or multi-use pouch which in the art is also referred to as a sachet. Sachets may also be in the form of shaped, stand-up, retort, box, slider, and zipper sachets, and the like.

The flexible body of the container may be made with any of a variety of suitable materials. In certain embodiments, the flexible body will be formed out of polymers or plastics used in the packaging of consumer products. These include, but are not limited to, polycarbonate (PC), polyethylene terephthalate (PET), high density polyethylene (HDPE), low density polyethylene (LDPE), polypropylene (PP), and polyvinyl chloride (PVC) and combinations thereof. In the case of retort pouches or sachets, the inner layer may be formed of thin metal foils. In some embodiments, the flexible body will be formed by coextruding inner and outer layers.

In some embodiments, the polymers or plastics used to form the flexible body can be made of biodegradable or dissolvable polymers. Biodegradable polymers are a specific type of polymer that breaks down after its intended purpose to result in natural byproducts such as gases ($CO_2$, $N_2$), water, biomass, and inorganic salts. Biodegradable polymers are found both naturally and synthetically made, and largely consist of ester, amide, and ether functional groups. Biodegradable polymers that can be used include, but are not limited to: polyhydroxyalkanoates (PHAs) like the poly-3-hydroxybutyrate (PHB), polyhydroxyvalerate (PHV) and polyhydroxyhexanoate (PHH); polylactic acid (PLA); polybutylene succinate (PBS), polycaprolactone (PCL), and polyanhydrides (PAH). Dissolvable polymers that can be used include, but are not limited to: polyvinyl alcohol (PVOH); most of the starch derivatives; cellulose esters like cellulose acetate and nitrocellulose and their derivatives (celluloid).

The containers of the present invention may comprise any suitable spout through which fluid, material, or product may be introduced into, or removed from, the inside of the container. The spout may be connected to the flexible body of the container by a number of known means, several of which will be described later. The spout suitable for use in the present invention may be made of any suitable material. Examples of such materials include the polymers or plastics used in the packaging of consumer products. These include, but are not limited to, high density polyethylene (HDPE), low density polyethylene (LDPE), polypropylene (PP), polycarbonate (PC), polyethylene terephthalate (PET), and polyvinyl chloride (PVC). In some embodiments, the spout may be formed of metal, or the biodegradable or dissolvable polymers discussed above.

For any given embodiment, at least one spout of the present invention is sized to have a water filter element of the present invention disposed therein and attached thereto. In some embodiments, the water filter element will be permanently attached to the spout. Methods such as ultrasonic welding, thermal fusing, or permanent adhesives may be used to permanently attached the water filter element to the spout. In other embodiments, the water filter element will be removably attached to the spout. Any suitable connection elements for removably connecting the water filter element to the port may be used. For example, the port and water filter element may comprise connection elements such as screw threads, snap-fit connection elements, resistant fit elements, and the like.

The water filter element of the present invention may comprise any suitable filter. Suitable filters for use in the present invention comprise filters capable of filtering out a variety of health-related contaminants such as organic contaminants or infectious microorganisms found in the water supplies. Infectious microorganisms found in the water supplies include bacteria, such as *Shigella, Escherichia coli, Vibrio*, and *Salmonella*, and protozoans, such as *Entamoeba, Giardia*, and *Cryptosporidium*.

Applicants have identified a variety of filtering materials which may be used. Reverse osmosis (RO) or nano-filtration (NF) membranes may be used, though these require high upstream pressure to drive water through them. In certain embodiments where there is a desire for using a filter that does not require significant pressure to drive water through the filter, a filter comprising nano-filter media (NFM) such as Boehmite (aluminum oxide hydroxide) fiber nano-particles may be used. In other embodiments, nano-fibers on micro-glass fiber carries may be used as a filter media. Filters comprising carbon nano-tubes may also be used in still other embodiments.

In certain particularly preferred embodiments, it is preferred that the filter would allow the user to fill the containers of the present invention in a reasonable amount of time using only gravity flow or hand squeezing of a squeezable water source (e.g. a water bottle). In some embodiments, container fill time is about ten minutes or less, or about five minutes or less, or about three minutes or less or about one minute or less.

The applicants have found that using Boehmite filters from Ahlstrom Corporation (Helsinki, Finland) and a 15 cm head of water pressure (about 150 Pa) in a two-liter water PET bottle, a flow rate of 0.75 ml/(min*$cm^2$) can be obtained. They have also found that by squeezing the two-liter bottle, a flow rate of about 20 ml/(min*$cm^2$) can be obtained. At this flow rate, and with a spout area of about 5 cm$^2$, a 100 ml container can be filled in about a minute. According to certain embodiments, the filter of the present invention has a flow rate of about 5 ml/(min*cm$^2$) or greater, including, about 10 ml/(min*cm$^2$) or greater, about 15 ml/(min*cm$^2$) or greater, or about 20 ml/(min*cm$^2$) or greater when water is squeezed from a two-liter water PET bottle through the filter using a grip strength of about 30 kilograms. According to certain embodiments, the filter of the present invention has a flow rate of about 5 ml/(min*cm$^2$) or greater, including, about 10 ml/(min*cm$^2$) or greater, about 15 ml/(min*cm$^2$) or greater, or about 20 ml/(min*cm$^2$) or greater when water is squeezed from a two-liter water PET bottle through the filter using a grip strength of about 40 kilograms. According to certain embodiments, the filter of the present invention has a flow rate of about 5 ml/(min*cm$^2$) or greater, including, about 10 ml/(min*cm$^2$) or greater, about 15 ml/(min*cm$^2$) or greater, or about 20 ml/(min*cm$^2$) or greater when water is squeezed from a two-liter water PET bottle through the filter using a grip strength of about 50 kilograms. According to certain embodiments, the filter of the present invention has a flow rate of about 5 ml/(min*cm$^2$) or greater, including, about 10 ml/(min*cm$^2$) or greater, about 15 ml/(min*cm$^2$) or greater, or about 20 ml/(min*cm$^2$) or greater when water is squeezed from a two-liter water PET bottle through the filter using a grip strength of about 60 kilograms.

The water filter element of the present invention may comprise any suitable attachment element for connecting to a water source. Suitable attachment elements may comprise screw threads, snap-fit connection elements, resistant fit elements, and the like. In certain preferred embodiments, the attachment element comprises screw threads sized to fit and engage with the screw threads of a water hose and/or a water bottle to connect thereto. In certain preferred embodiments, the attachment element of the removable water filter comprises a female attachment element and the connecting element on the water source is a corresponding male connection element. For example, in preferred embodiments wherein the water source is a hand held bottle containing water, the screw threads commonly found around the neck of the hand held bottle may be screwed into a female attachment element of the water filter element to engage the screw threads therein and connect the bottle to the water filter element.

Those of skill in the art will recognize that the term "hand held bottle" refers to any of a variety of commercially available bottles that can be held in the hand and may be used in general as a source of drinking water (or other fluid). Hand held bottles may be of any suitable size including, for example, bottles sized to hold from about two liters or less, including from about one liter or less, from about 500 milliliter or less, from about 250 milliliter or less. Preferably, the hand held bottle is made from a flexible material, and may be squeezed by hand to help expel the fluid contained therein. Examples of certain hand held bottles include commercially available plastic twelve ounce, twenty ounce, one liter, two liter (or other commercially available sizes around the world) bottles of water, soda, or other fluids intended for drinking, or other similar sized bottles for other products that have been emptied and may then be filled with water for use in the present invention.

In certain embodiments, the concentrate in the container of the present invention may be substantially free of preservatives. Examples of preservatives include, but are not limited to, parabens, quaternary ammonium species, phenoxyethanol, benzoates, DMDM hydantoin, and the like. As used herein "substantially free of preservatives" means less than 0.5% by weight of a product of preservatives, including, for example, less than 0.1%, less than 0.05%, less than 0.01% by weight of the product of preservatives, or in certain embodiments the product is free of preservatives.

Accordingly, in certain embodiments, the present invention provides for methods of reconstituting a concentrated product comprising providing a flexible container containing a concentrate, attaching a water source to the attachment element of the flexible container, and forcing water through the filter element of the container and into the container to reconstitute a concentrate therein.

Any of the suitable elements as described above may be used in the methods of the present invention. In certain embodiments, the water source is a capable of being held and squeezed in the hand, and the step of forcing water through the filter element comprises squeezing the water source by hand to force water through the filter element.

In certain embodiments, the method comprises forcing a predetermined and/or desired amount of water into the container to reconstitute the concentrate. Such predetermined/desired amount may be sufficient water to fill the flexible container, or may be an amount indicated by a visible indicator (e.g. a fill line or the like) or other indicator in or on the container. Those of skill in the art will readily understand the use of a visible fill indicator (such as a fill line or other indicator) to indicate to a user when sufficient water has been added to the flexible container to reconstitute the concentrate. In certain embodiments, the reconstituted concentrate made in accord with the present invention may be stored prior to use and/or when designed for multiple uses, the product may be stored in between uses.

In certain embodiments of the present invention, the product resulting from reconstituting the concentrate may be used by dispensing the product back through the spout used to introduce water to the concentrate. Such dispensing may be done with the filter in place or removed. In certain embodiments the filter is removed. In these embodiments, the product may be dispensed by removing the filter element from the spout and dispensing the reconstituted product. In embodiments wherein the flexible container contains more than one spout, the resulting product may be dispensed back out through the spout used to introduce water, or may instead be dispensed through a second spout configured to allow reconstituted product to be dispensed therethrough.

In certain embodiments, after reconstituting the product, the removable filter may be removed from the spout while the removable filter remains attached to the water source. In this way, water from the water source may be forced through the removed filter element to provide filtered and/or potable water outside of the flexible container for drinking or other purposes. In other embodiments, after reconstituting the product, the removable filter element may be removed from the spout and the water source, optionally cleaned, and then attached to either the same or a different water source. In this way, water from the water source may be forced through the removed filter element to provide filtered and/or potable water outside of the flexible container for drinking or other purposes.

Figure 2:
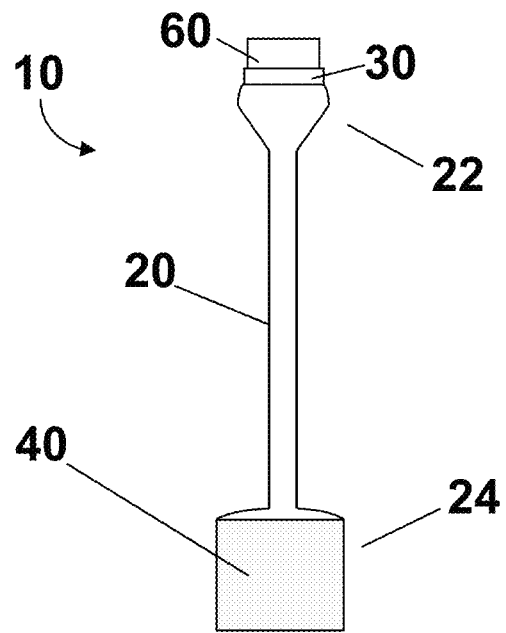
FIG. 2 is a side view of the flexible package embodiment of FIG. 1.

Further illustration of certain embodiments of the device and method of the present invention are now described in a non-limiting manner with reference to the drawings. FIGS. 1 and 2 show a flexible package according to an embodiment of the present invention. FIG. 1 is a front view of package 10 comprising flexible container or pouch 20 with proximal 22 and distal 24 ends. Spout 30 is located on proximal end 22 of flexible container 20. Water filter element 60 is disposed in spout 30. Flexible container 20 is partially filled with concentrated consumer product 40. Consumer product 40 may be in the form of a concentrated liquid, a loose or compressed powder, tablets, or a combination of forms. FIG. 2 is a side view of flexible package 10, showing a narrow section in flexible container 20 between proximal 22 and distal 24 ends.

Figure 3A:
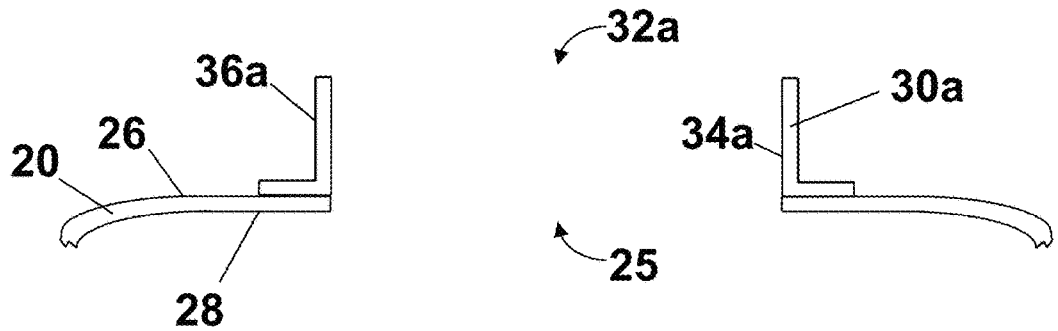
FIG. 3a is a side cross-sectional view of a first embodiment of a spout and its attachment to the flexible package embodiment of FIG. 1.
Figure 3B:
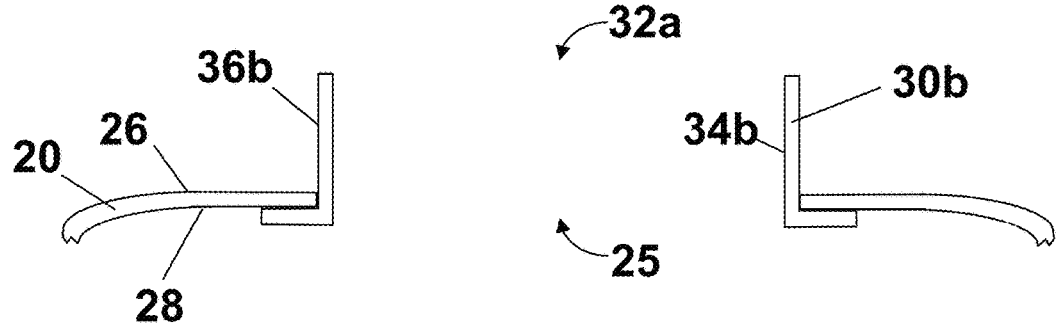
FIG. 3b is a side cross-sectional view of a second embodiment of a spout and its attachment to the flexible package embodiment of FIG. 1.
Figure 3C:
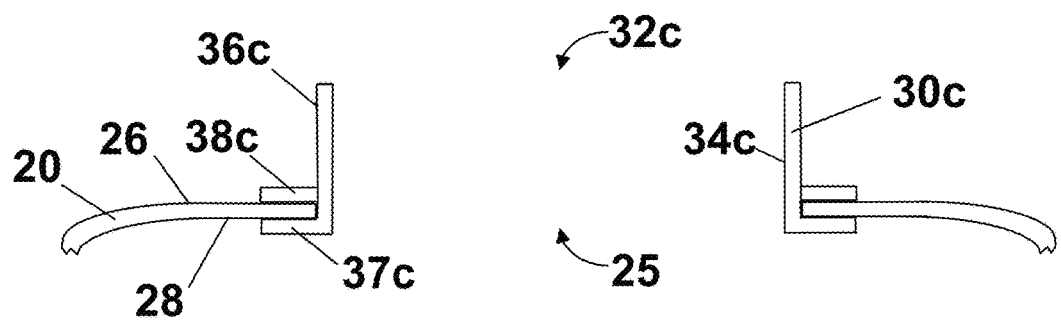
FIG. 3c is a side cross-sectional view of a third embodiment of a spout and its attachment to the flexible package embodiment of FIG. 1.

The packages of the present invention may comprise any suitable spout through which fluid, material, or consumer product may be introduced into, or removed from, the inside of the container. FIG. 3a is a side cross-sectional view of a first embodiment of a spout 30a and its attachment to flexible container 20. The figure shows spout 30a with spout opening 32a, and inner and outer spout walls, 34a and 36a, respectively. The figure also shows flexible container 20 with container opening 25, and outer and inner container walls, 26 and 28, respectively. Spout 30a is attached to outer wall 26 of flexible container 20, and inner wall 34a surrounds container opening 25 such that fluid or other material may flow through the spout opening 32a into and out of container 20 through container opening 25. In a second embodiment, shown in FIG. 3b, spout 30b may be attached to inner wall 28 of flexible container 20, and extend through and out of container 20 through container opening 25. In this embodiment, inner wall 34b of spout 30b defines spout opening 32b through which material may flow into and out of flexible container 20. In a third embodiment, shown in FIG. 3c, spout 30c may comprise a first spout portion 37c attached to inner wall 28 of the flexible container 20. A locking ring 38c is attached to the outer wall 26 of spout 30c to hold spout 30c in place. Here, inner wall 34c of spout 30c defines spout opening 32c through which material may flow into and out of flexible container 20.

Figure 4:
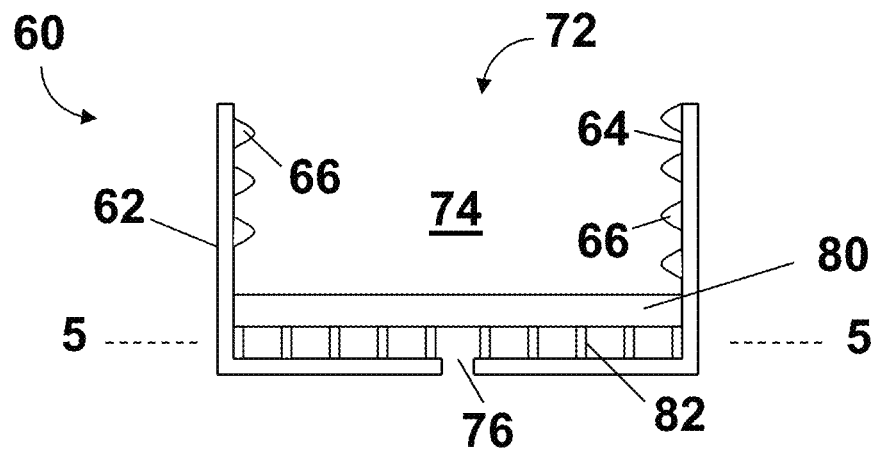
FIG. 4 is a side cross-sectional view of a first embodiment of a water filter element of the flexible package embodiment of FIG. 1.
Figure 5:
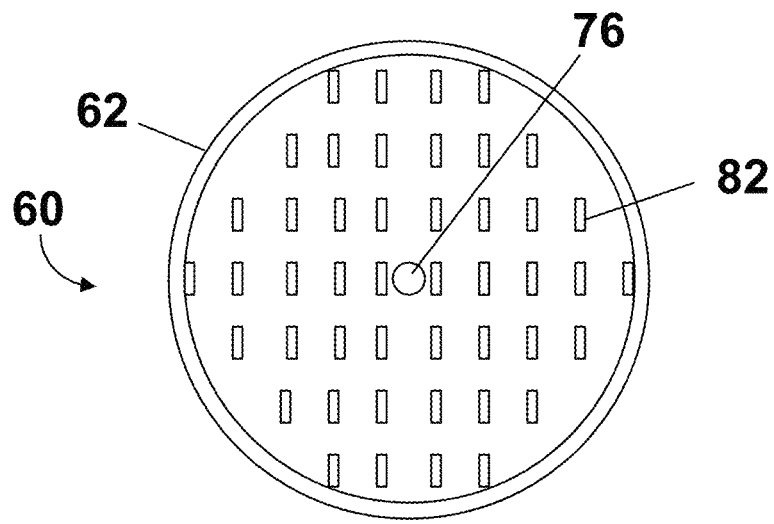
FIG. 5 is a top cross-sectional view of a section of the water filter element of FIG. 4 taken along the 5-5 plane.

FIGS. 4 and 5 show a first embodiment of water filter element 60. FIG. 4 is a side cross-sectional view of filter element 60, which includes outer surface 62 and inner surface 66. Inner surface 66 has attachment means 68, shown as screw threads. Filter element 60 has filter opening 72. The walls of water filter element 60 define open volume 74 in which is disposed filter 80. Contaminated water will enter water filter element 60 through open volume 74, pass through filter 80, and leave water filter element 60 through filter port 76 as clean water.

In the embodiment shown in FIGS. 4 and 5, filter 80 is held in place by filter supports 82. Other embodiments of support for filter 80 include spacers or "O"-rings, and the like.

FIG. 5 is a top cross-sectional view of a section of the removable water filter element of FIG. 4 taken along the 5-5 plane. The figure shows filter supports 82 and filter port 76. In the embodiment shown, a single filter port 76 is shown with a circular cross-section. In other embodiments, there may be multiple filter ports 76, and they may have a number of other cross-sectional shapes such as oval, square, rectangular, etc. In the embodiment shown in FIG. 5, numerous filter supports 82 with rectangular cross-sectional shapes are shown. In other embodiments, filter supports 82 may have a number of other cross-sectional shapes such as circular, oval, square, etc.

Though not shown, a closure device for filter element 60 may be employed prior to use of package 10. In some embodiments, a cap may engage with filter element 60 by means of screws threads, a snap-fit or a resistant fit. In other embodiments, a plug that fits into the inner surface 66 of filter element 60 and is connected to filter element 60 via attachment means 68, may be used. In yet other embodiments, a foil or plastic membrane may be used to seal filter element 60 prior to use of package 10.

Figure 6:
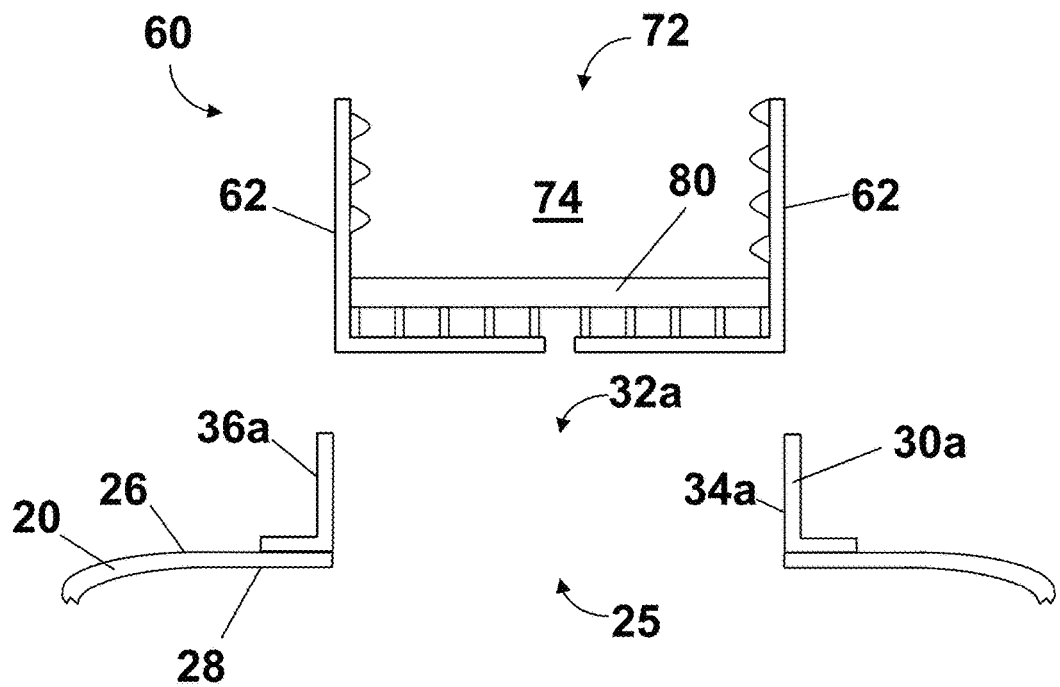
FIG. 6 is a side cross-sectional view of the water filter element as shown in FIG. 4 prior to attachment to the flexible package embodiment of FIG. 1.
Figure 7:
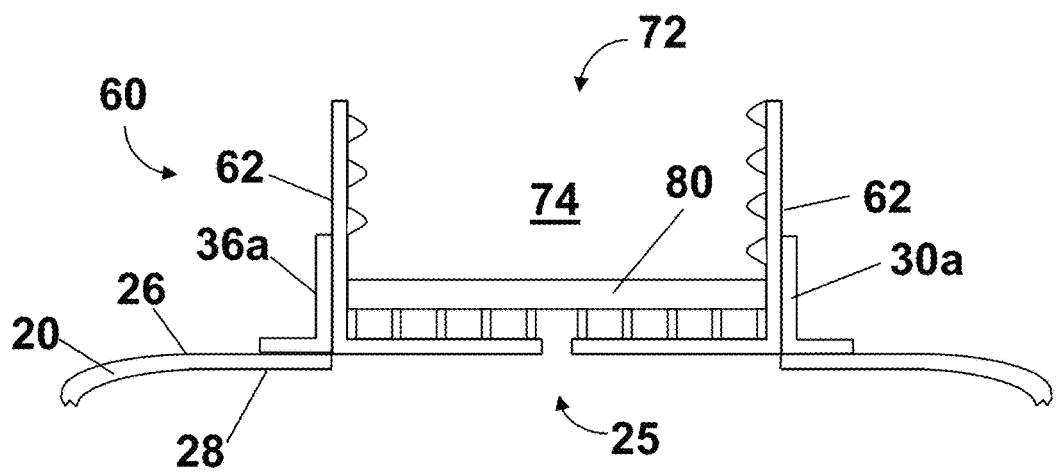
FIG. 7 is a side cross-sectional view of the water filter element as shown in FIG. 4 after attachment to the flexible package embodiment of FIG. 1.

Water filter element 60 is disposed in, and attached to, spout 30. FIGS. 6 and 7 show one embodiment of the steps used to attach water filter element 60 to spout 30a. FIG. 6 is a side cross-sectional view of water filter element 60 and spout 30a prior to their attachment. The figure shows water filter element 60 sized to fit into spout 30a such that outer surface 62 of water filter element 60 contacts inner spout walls 34a. FIG. 7 is a side cross-sectional view of the water filter element 60 and spout 30a after their attachment. In one embodiment, a resistance fit can keep water filter element 60 from separating from spout 30a. In other embodiments, adhesive can be applied to either or both outer surface 62 of water filter element 60 and inner spout walls 34a to keep the parts from separating. In some embodiments, water filter element 60 will be permanently attached to spout 30a. Methods such as ultrasonic welding, thermal fusing, or permanent adhesives may be used to permanently attached water filter element 60 to spout 30a. In other embodiments, water filter element 60 may be removably attached to spout 30a. Snap-fit and screw thread attachment means may allow water filter element 60 to be removably attached to spout 30a.

Figure 8:
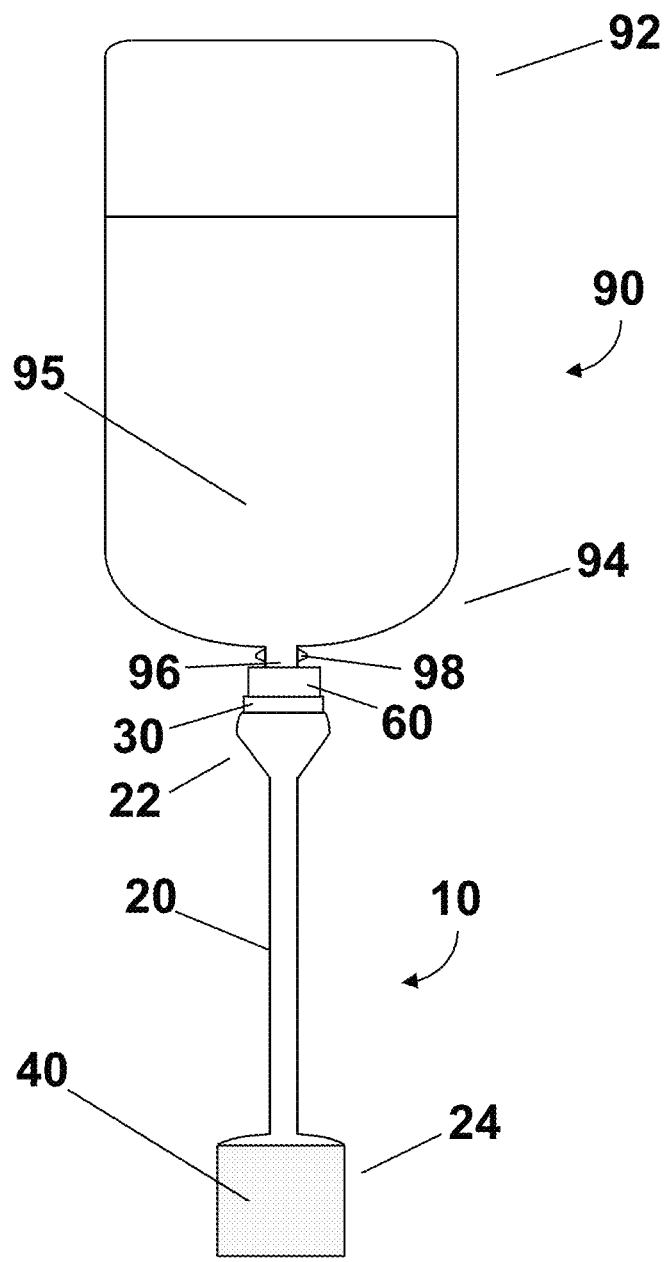
FIG. 8 is a schematic view of a flexible package according of the present invention coupled to a water source prior to being filled.
Figure 9:
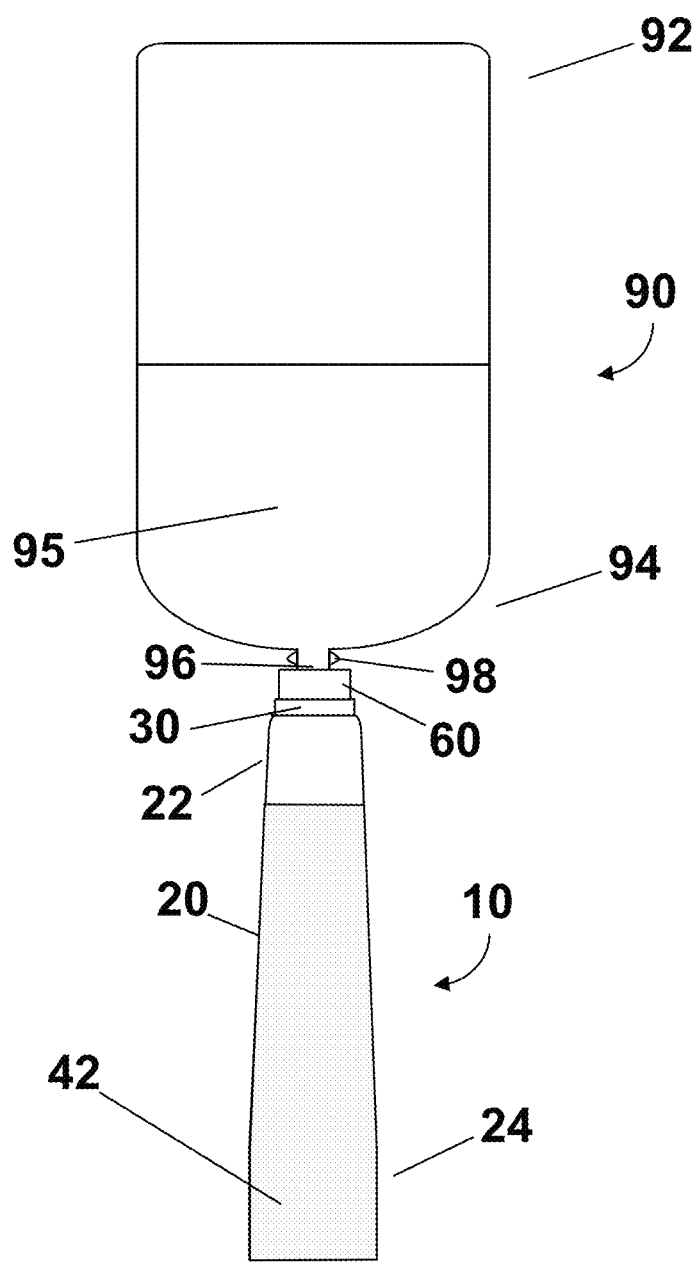
FIG. 9 is a schematic view of a flexible package according of the present invention coupled to a water source after being filled.

FIGS. 8 and 9 show one embodiment of a method of use of flexible package 10 according to an embodiment of the present invention. FIG. 8 is a schematic view of package 10 coupled to a removable water source 90 prior to being filled. In this embodiment, water source is a bottle 90 with proximal 92 and distal 94 ends containing contaminated water 95. Neck 96 is located on distal 94 end of bottle 90 and has screw threads 98 as a means to attach to flexible package 10. In this embodiment, screw threads 98 of bottle 90 and screw threads 68 located on inner surface 66 of filter element 60 are sized so that screw threads 98 of bottle 90 engage with screw threads 68 of filter element 60. Plastic water bottles have standard screw thread profiles, and screw threads 68 of filter element 60 can be designed to fit the standard screw thread profiles.

In other embodiments, neck 96 of bottle 90 may engage with filter element 60 by means of a snap-fit or resistant fit.

In yet other embodiments, water source 90 could be in the form of a conduit such as a pipe or hose through which contaminated water 95 is pumped. Pipe or hose could have screw threads sized to be able to engage with screw threads 68 located on inner surface 66 of filter element 60. In still other embodiments, pipe or hose may engage with filter element 60 by means of a snap-fit or resistant fit.

In FIG. 8, flexible container 20 with concentrated consumer product 40 is shown in flattened configuration. FIG. 9 is a schematic view of package 10 coupled to a water source 90 after being filled. Flexible container 20 with reconstituted consumer product 42 is shown in distended configuration.

In one embodiment method of using flexible package 10 according of the present invention, flexible package 10 containing concentrated consumer product 40 is first coupled to contaminated water source. Contaminated water source is then pressurized to force contaminated water through filter element 60 and into flexible container 20. In the embodiment shown in FIGS. 8 and 9, where water source 90 is a bottle 90, pressure may be applied to bottle 90 by squeezing bottle 90. In embodiments using pipes or hoses, upstream pressure could be applied in the pipe or hose to force contaminated water through filter element 60 and into flexible container 20.

The amount of contaminated water passed through filter element 60 and into flexible container 20 will depend on the amount of water needed to dilute concentrated consumer product 40 to properly reconstituted consumer product 42. There are many ways to determine the amount of water needed to dilute concentrated consumer product 40 to properly reconstituted consumer product 42. For example, the use of indicia marked on flexible container 20 is one method. As shown in FIG. 9, distended configuration flexible container 20 is another indicator that sufficient water has been added to flexible container 20 to convert concentrated consumer product 40 to properly reconstituted consumer product 42.

Once sufficient water is passed through filter element 60 and into flexible container 20, flexible package 10 is uncoupled from contaminated water source. Properly reconstituted consumer product 42 is now ready for use. To use consumer product 42, user removes water filter element 60 from spout 30 and disperses consumer product 42 through spout 30. Water filter element 60 may be removed from spout 30 by a number of means. In one embodiment, the user can punch through water filter element 60 using punching tool. If water filter element 60 is removably attached to spout 30, the user may easily remove filter element 60 from spout 30 and disperse consumer product 42 through spout 30.

Once consumer product 42 is fully dispersed from package 10, package 10 can be discarded. If the elements of package 10 are made of biodegradable or dissolvable polymers, disposal of package 10 will not contribute to the problems of trash accumulation in many parts of the world.

In embodiments using a removable water filter element, the filter element may have the ability to be reusable. In these embodiments, the water filter element may be removed from a first flexible container/spout package and disposed in a second package. In these embodiments, kits can be sold which contain a single, reusable water filter element and multiple packages comprising flexible containers/spouts. In these embodiments, a single filter can be used with up to two, or four, or six, or twelve, or twenty four or more packages comprising flexible containers/spout configurations. In some embodiments, the individual flexible containers/spout configurations can each be single-use sachets.

Figure 10:
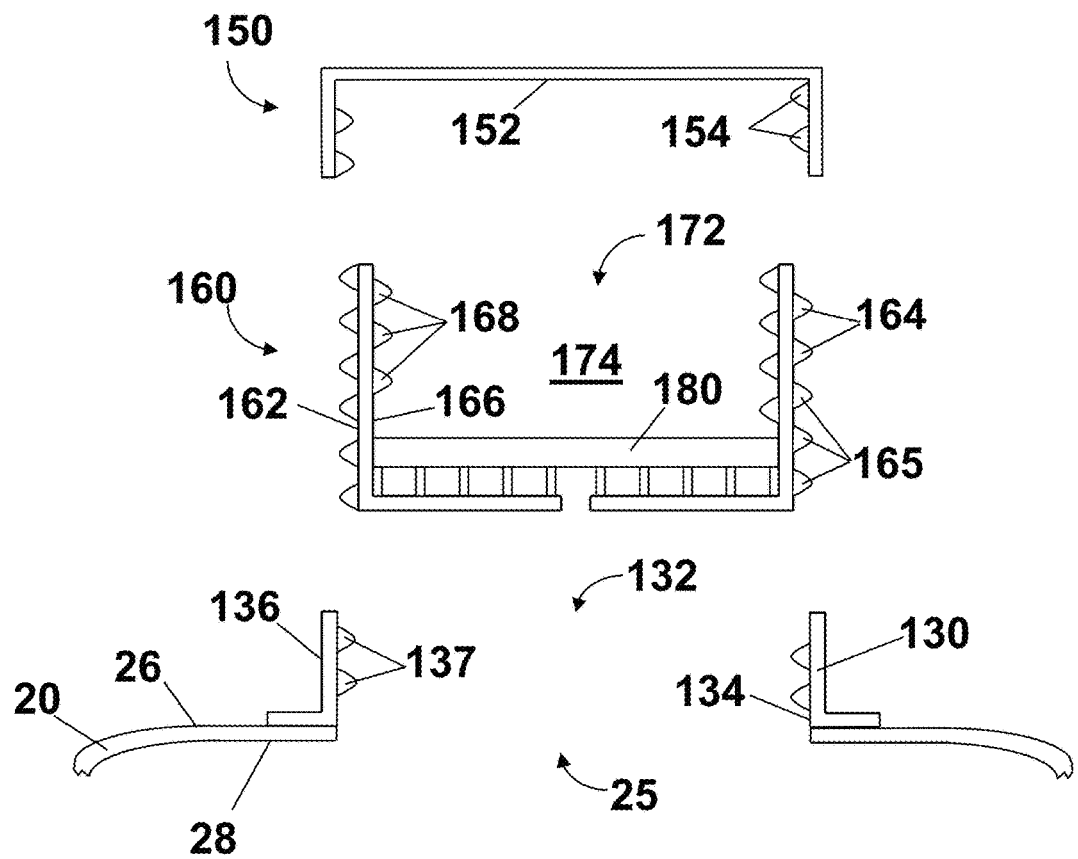
FIG. 10 is a side cross-sectional view of an embodiment of a removable water filter element prior to attachment to the flexible package embodiment of FIG. 1.

In some embodiments, removable water filter elements can find a second important use in locations, such as developing countries or wilderness area, where water sources are often contaminated. The removable water filter element can be attached to a hand held bottle, filled with contaminated water and used to filter out said contaminations to make the water potable. FIG. 10 is a side cross-sectional view of an embodiment of a removable water filter element 160 prior to assembly with spout 130 of a flexible package embodiment of the present invention.

The figure shows removable water filter element 160, which includes outer surface 162 and inner surface 166. Outer surface 162 has first attachment means 164, here shown as screw threads, as well as second attachment means 165, also shown as screw threads. Inner surface 166 has third attachment means 168, also shown as screw threads. The walls of removable water filter element 160 define open volume 174 in which is disposed filter 180. Filter 180 is held in place, in this embodiment, by filter supports 182. Contaminated water will enter water filter element 160 through open volume 174, pass through filter 180, and leave water filter element 160 has through filter port 176 as clean water.

Figure 11:
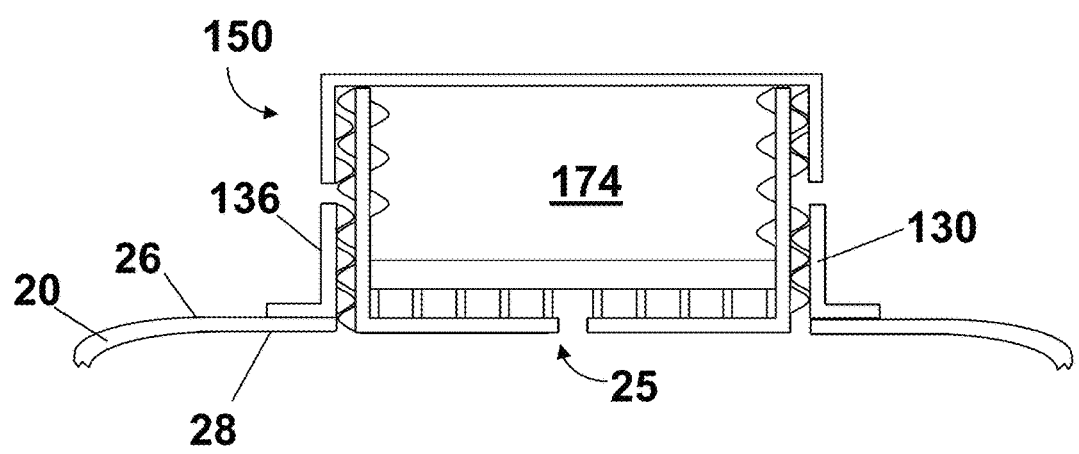
FIG. 11 is a side cross-sectional view of an embodiment of a removable water filter element after attachment to the flexible package embodiment of FIG. 1.

In this embodiment, cap 150 is designed to act as a closure device for filter element 160. Cap 150 has means of attachment 154, in this embodiment shown as screws threads 154, located on inner surface 152 of cap 150. In this embodiment, screw threads 164 located on outer surface 162 of filter element 160 and screws threads 154 on cap 150 are sized so that screws threads 154 on cap 150 engage with screw threads 164 of filter element 160. FIG. 11 shows cap 150 attached to removable water filter element 160. In other embodiments, cap 150 may engage with water filter element 160 by means of a snap-fit or resistant fit.

FIG. 10 also shows another spout embodiment. The figure shows spout 130 with spout opening 132, and inner and outer spout walls, 134 and 136, respectively. Inner spout walls 134 have attachment means in the form of screw threads 137. The figure also shows flexible container 20 with container opening 25, and outer and inner container walls, 26 and 28, respectively. Spout 130 is attached to outer wall 26 of flexible container 20, and inner wall 134 surrounds container opening 25 such that fluid or other material may flow through the spout opening 132 into and out of container 20 through container opening 25.

FIG. 11 shows removable water filter element 160 disposed in spout 130 of flexible container 120, and screws threads 137 on spout 130 engage with screw threads 165 of water filter element 160. Removable water filter element 160 is now removably attached to spout 130. In other embodiments, snap-fit or resistant fit may be used to couple water filter element 160 to spout 130 of flexible container 20.

As described earlier, flexible container may now be filled with contaminated water to dilute concentrated consumer product. As described in FIGS. 8 and 9, water source is a bottle 90 with proximal 92 and distal 94 ends containing contaminated water 95. Neck 96 is located on distal 94 end of bottle 90 and has screw threads 98 as a means to attach to flexible package 10. In this embodiment, screw threads 98 of bottle 90 and screw threads 168 located on inner surface 166 of filter element 160 are sized so that screw threads 198 of bottle 190 engage with screw threads 168 of filter element 160. In other embodiments, neck 96 of bottle 90 may engage with filter element 160 by means of a snap-fit or resistant fit.

In this embodiment method of using flexible package 10 according of the present invention, flexible package 10 containing concentrated consumer product 40 is first coupled to contaminated water source. Contaminated water source is then pressurized to force contaminated water through filter element 160 and into flexible container 20. As in the embodiment shown in FIGS. 5 and 6, pressure may be applied to bottle 90 by squeezing bottle 90, passing contaminated water 95 through filter element 160 and into flexible container 20.

In this embodiment, once sufficient water is passed through removable filter element 160 and into flexible container 20, flexible package 10 is uncoupled from contaminated water source while filter element 160 remains coupled to contaminated water source. This is accomplished when screw threads 165 are disengaged from matching screw threads located inside port 30 of flexible package 10. Now, filter element 160 remains coupled to bottle 90 via the engagement of screw threads 98 of bottle 90 and screw threads 168 of filter element 160.

Figure 12:
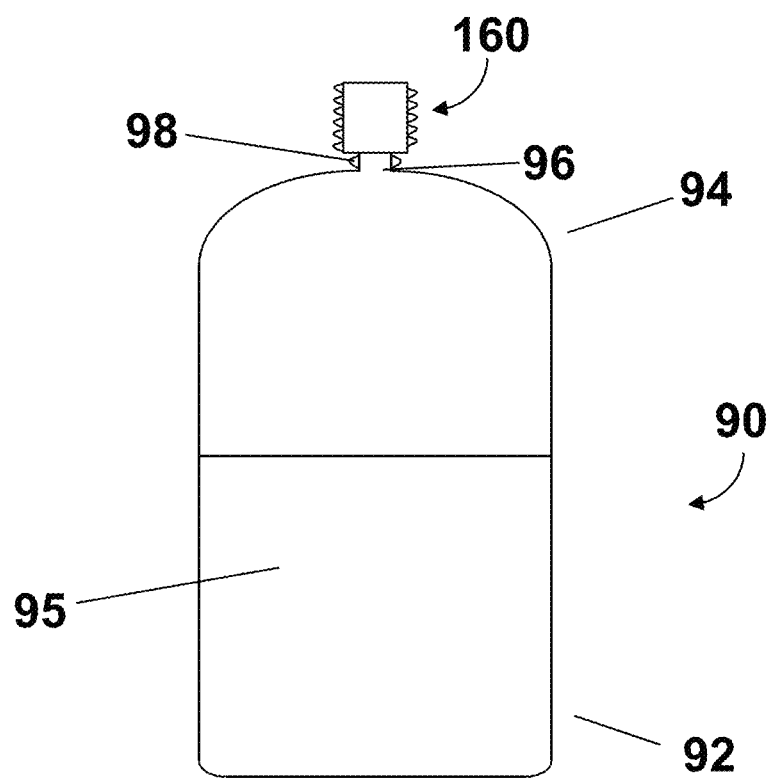
FIG. 12 is a schematic view of the removable water filter element of FIG. 10 coupled to a water source after being removed from a flexible package embodiment of the present invention.

FIG. 12 is a schematic view of water filter element 160 of FIG. 10 coupled to a water bottle 90 after being removed from flexible package 10. At this point, the user now is able to obtain clean water for drinking, washing, or other uses by using removable water filter element 160 to filter contaminated water 95 in bottle 90.

Though not shown, a cap with matching screw threads can engage with screw threads 165 on removable water filter element 160 to seal water bottle 90 between uses.

Figure 13:
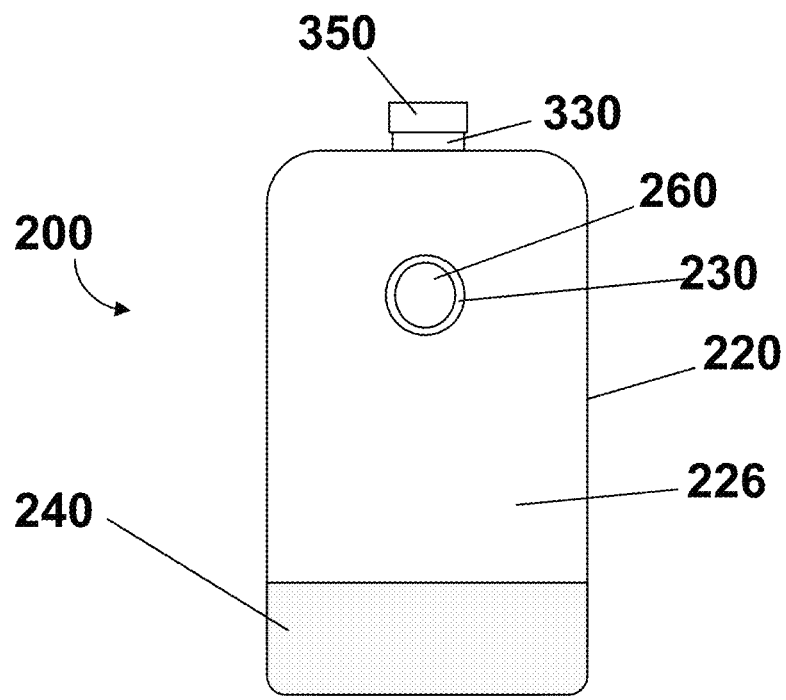
FIG. 13 is a front view of a flexible package according to a second embodiment of the present invention.
Figure 14:
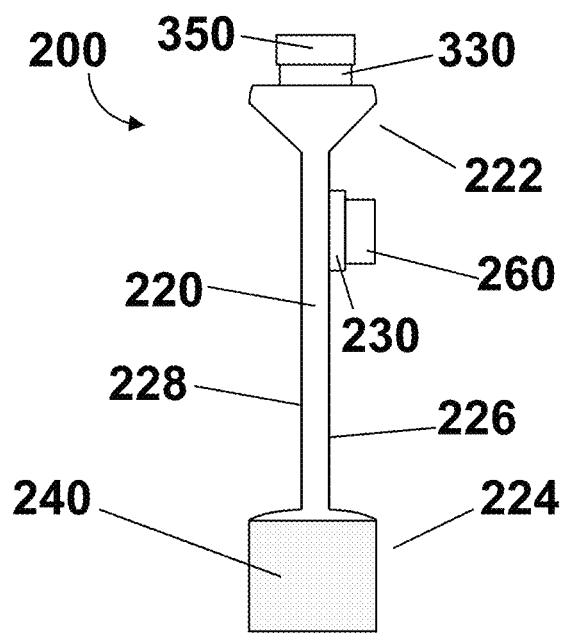
FIG. 14 is a side view of the flexible package embodiment of FIG. 13.

FIGS. 13 and 14 show a flexible package according to a second embodiment of the present invention. FIG. 13 is a front view of package 200 comprising flexible container or pouch 220 with proximal 222 and distal 224 ends, as well as first face 226 and second face 228. First spout 230 is located on first face 226 of flexible container 220. Second spout 330 is located on proximal end 222 of flexible container 220. Although first spout 230 is located on first face 226 of flexible container 220, it may be located on second face 228 of flexible container 220. Also, it is to be understood that although this embodiment shows two spouts, there may be more than two spouts located on any of proximal 222 and distal 224 ends, as well as first face 226 and second face 228 of flexible container 220.

Water filter element 60 is disposed in first spout 230, and cap 350 is shown disposed on second spout 330. It is to be understood that in some embodiments, water filter element 60 may be disposed in second spout 330, while cap 350 may be disposed on first spout 230. Also, in some embodiments, there may be no cap, or multiple caps.

Flexible container 220 is partially filled with concentrated consumer product 240. As mentioned earlier, consumer product 240 may be in the form of a concentrated liquid, a loose or compressed powder, tablets, or a combination of forms. FIG. 14 is a side view of flexible package 200, showing a narrow section in flexible container 220 between proximal 222 and distal 224 ends. Though shown as relatively flat in FIGS. 13 and 14, flexible container 220 may be in a folded configuration to save space in storage.

Figure 15:
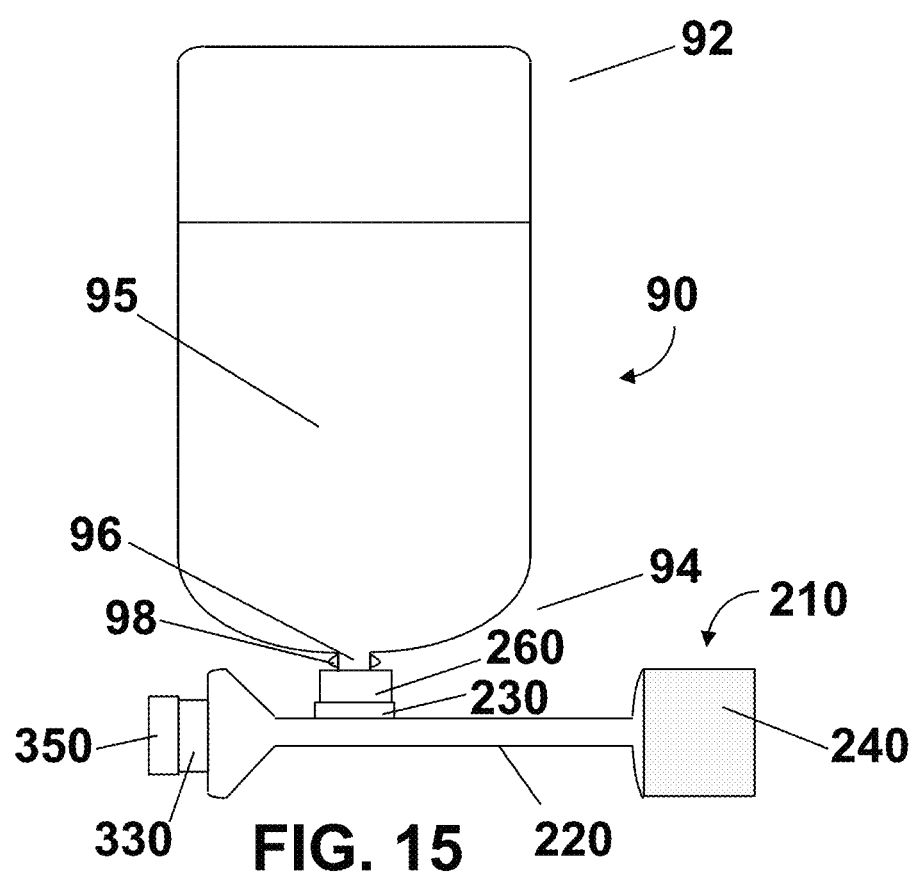
FIG. 15 is a schematic view of the second embodiment of the flexible package according of the present invention coupled to a water source prior to being filled.
Figure 16:
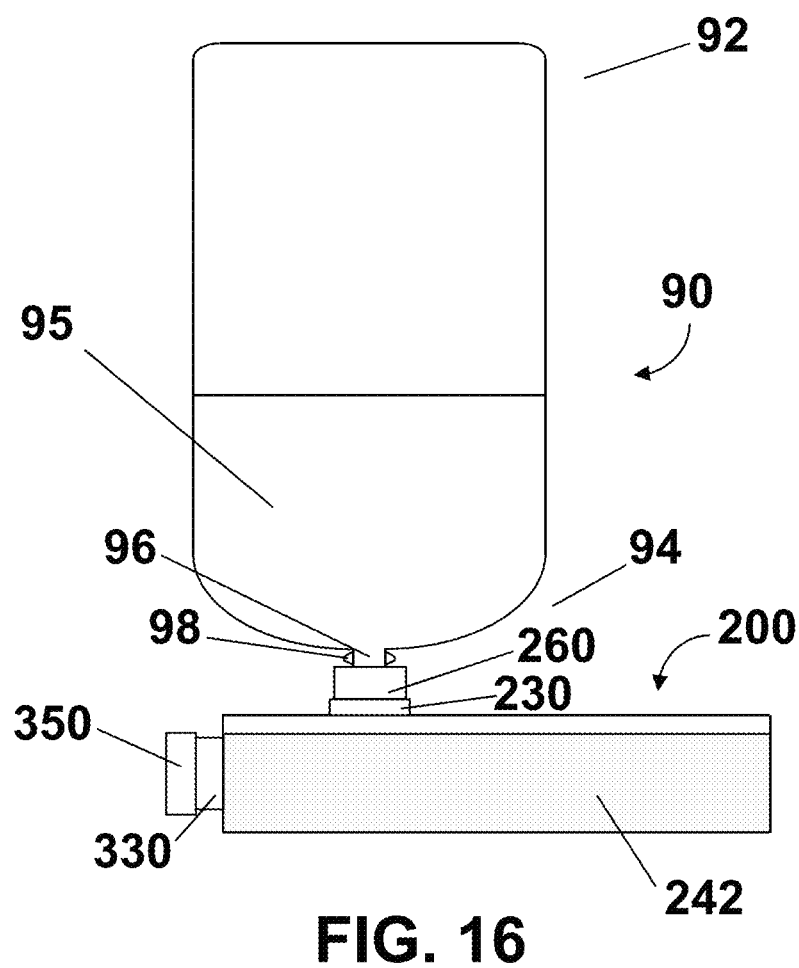
FIG. 16 is a schematic view of the second embodiment of the flexible package according of the present invention coupled to a water source after being filled.

FIGS. 14 and 15 show one embodiment of a method of use of flexible package 200 according to an embodiment of the present invention. FIG. 14 is a schematic view of package 200 coupled to a removable water source 90 prior to being filled. Water source is a bottle 90 with proximal 92 and distal 94 ends containing contaminated water 95. Neck 96 is located on distal 94 end of bottle 90 and has screw threads 98 as a means to attach to flexible package 10. In this embodiment, screw threads 98 of bottle 90 and screw threads 68 located on inner surface 66 of filter element 60 (see FIGS. 6 and 7) are sized so that screw threads 98 of bottle 90 engage with screw threads 68 of filter element 60. Plastic water bottles have standard screw thread profiles, and screw threads 68 of filter element 60 can be designed to fit the standard screw thread profiles.

In other embodiments, neck 96 of bottle 90 may engage with filter element 60 by means of a snap-fit or resistant fit.

In yet other embodiments, water source 90 could be in the form of a conduit such as a pipe or hose through which contaminated water 95 is pumped. Pipe or hose could have screw threads sized to be able to engage with screw threads 68 located on inner surface 66 of filter element 60. In still other embodiments, pipe or hose may engage with filter element 60 by means of a snap-fit or resistant fit.

In FIG. 14, flexible container 220 with concentrated consumer product 240 is shown in flattened configuration. FIG. 15 is a schematic view of package 200 coupled to a water source 90 after being filled. Flexible container 220 with reconstituted consumer product 242 is shown in distended configuration.

In one embodiment method of using flexible package 200 according of the present invention, flexible package 200 containing concentrated consumer product 240 is first coupled to contaminated water source. Contaminated water source is then pressurized to force contaminated water through filter element 60 and into flexible container 220. In the embodiment shown in FIGS. 14 and 15, where water source 90 is a bottle 90, pressure may be applied to bottle 90 by squeezing bottle 90. In embodiments using pipes or hoses, upstream pressure could be applied in the pipe or hose to force contaminated water through filter element 60 and into flexible container 220.

The amount of contaminated water passed through filter element 60 and into flexible container 220 will depend on the amount of water needed to dilute concentrated consumer product 240 to properly reconstituted consumer product 242. There are many ways to determine the amount of water needed to dilute concentrated consumer product 240 to properly reconstituted consumer product 242. For example, the use of indicia marked on flexible container 220 is one method. As shown in FIG. 15, distended configuration flexible container 220 is another indicator that sufficient water has been added to flexible container 220 to convert concentrated consumer product 240 to properly reconstituted consumer product 242.

Once sufficient water is passed through filter element 60 and into flexible container 220, flexible package 200 is uncoupled from contaminated water source by disengaging neck 96 of bottle 90 from first spout 230. Properly reconstituted consumer product 242 is now ready for use.

In general, second spout 330 is configured to allow reconstituted consumer product 242 to be dispensed therethrough. In some embodiments, second spout 330 is designed so that water source 90 cannot connect with second spout 330. This is done to prevent user from connecting contaminated water to package 200 without water passing through water filter element 260 of first spout 230. In some embodiments, this may be done by designing second spout 330 with a non-round cross-section. Non-round cross-sections include, but are not limited to, as oval, square, diamond, or hexagonal. Second spout 330 may also be in a tapered configuration, such as frustoconical, to prevent the user from connecting contaminated water to package 200.

To use reconstituted consumer product 242, user removes cap 350 from second spout 330 and disperses reconstituted consumer product 242 through second spout 330. In embodiment not using a cap, the user can punch through second spout 330 using punching tool.

Once reconstituted consumer product 242 is fully dispersed from package 200, package 200 can be discarded. If the elements of package 200 are made of biodegradable or dissolvable polymers, disposal of package 200 will not contribute to the problems of trash accumulation in many parts of the world.

What is claimed is:

1. A method of reconstituting a concentrated product comprising:
    (a) providing a flexible container holding a concentrate, wherein said concentrate is a concentrate of a consumer product selected from the group consisting of lotions, soaps, shampoos, conditioners, body washes, facial cleansers, moisturizers, astringents, exfoliation products, microdermabrasion and peel products, skin rejuvenation products, anti-aging products, and UV protection products, wherein said flexible container comprises: (1) a flexible body holding said concentrate, (2) a spout, (3) a filter element disposed in said spout, wherein said filter element comprises a filter, wherein said filter is selected from the group consisting of nano-filter media; nano-fibers on micro-glass fiber carries; carbon nano-tubes; and mixtures thereof; and (4) an attachment element configured to attach to a water source;
    (b) attaching a water source to the attachment element of the flexible container; and (c) forcing water through the filter element of the container and into the container to form a reconstituted concentrate.

2. The method of claim 1 wherein said flexible container is in the form of a pouch.

3. The method of claim 2 wherein said water source is a hand held water bottle and said forcing step comprises squeezing said water bottle by hand to push water through the filter element and into said flexible container to reconstitute the concentrate.

4. The method of claim 3 wherein said flexible container is filled within a period of about five minutes or less.

5. The method of claim 4 wherein said container comprises a visible fill indicator and said forcing step comprises forcing sufficient water through the filter element such that the visible fill indicator indicates that the container is full.

6. The method of claim 1 further comprising the step of removing the filter element from said spout to dispense the reconstituted concentrate though said spout.

7. The method of claim 6 wherein said filter element remains attached to said water source when said filter element is removed from said spout.

8. The method of claim 1 wherein said flexible container comprises a second spout and said method further comprises the step of dispensing the reconstituted concentrate through said second spout.

9. The method of claim 1 wherein said concentrate is substantially free of preservatives.

10. The method of claim 1 wherein said forcing step comprises forcing water through said filter at a flow rate of about 10 ml/(min*cm$^2$) or greater.

11. The method of claim 10 wherein said forcing step comprises forcing water through said filter at a flow rate of about 20 ml/(min*cm$^2$) or greater.

12. The method of claim 7 further comprising the step of forcing water from the water source through the filter element removed from the spout to produce filtered water outside of said flexible container.

13. The method of claim 6 wherein said removed filter element is removed from the spout and the water source, optionally cleaned, and then attached to the same or a different water source.

14. The method of claim 12 wherein after said removed filter element is attached to the same or a different water source, water is forced therethrough to produce filtered water.

* * * * *